United States Patent
Lee et al.

(10) Patent No.: US 9,709,507 B2
(45) Date of Patent: Jul. 18, 2017

(54) APPARATUS AND METHOD FOR MEASURING CONTAMINATION OF FILTER

(71) Applicant: RAYTRON Co., LTD, Daejeon (KR)

(72) Inventors: Hyun Young Lee, Daejeon (KR); Ji Woong Jang, Daejeon (KR)

(73) Assignee: RAYTRON CO., LTD, Daejeon (KR)

( * ) Notice: Subject to any disclaimer, the term of this patent is extended or adjusted under 35 U.S.C. 154(b) by 12 days.

(21) Appl. No.: 14/712,975

(22) Filed: May 15, 2015

(65) Prior Publication Data

US 2016/0061747 A1 Mar. 3, 2016

(30) Foreign Application Priority Data

Sep. 3, 2014 (KR) .................. 10-2014-0116761

(51) Int. Cl.
*G01N 21/00* (2006.01)
*G01N 21/94* (2006.01)
(Continued)

(52) U.S. Cl.
CPC ......... *G01N 21/94* (2013.01); *B01D 46/0086* (2013.01); *G01N 21/255* (2013.01);
(Continued)

(58) Field of Classification Search
CPC .... G01J 3/02; G01J 3/513; G01J 3/51; G01N 15/1459; G01N 21/65
See application file for complete search history.

(56) References Cited

U.S. PATENT DOCUMENTS

| 7,012,685 B1* | 3/2006 | Wilson | ............... B01D 46/0086 356/239.1 |
| 2003/0011768 A1* | 1/2003 | Jung | ................... A61B 5/0088 356/326 |

(Continued)

FOREIGN PATENT DOCUMENTS

| JP | 07-280951 A | 10/1995 |
| JP | 2014-092477 A | 5/2014 |

(Continued)

OTHER PUBLICATIONS

Aug. 10, 2015, Korean Office Action for related KR application No. 10-2014-0116761.

*Primary Examiner* — Tarifur Chowdhury
*Assistant Examiner* — Md M Rahman
(74) *Attorney, Agent, or Firm* — Paratus Law Group, PLLC (57) ABSTRACT

Provided are an apparatus and method for measuring contamination of a filter. The filter contamination measuring apparatus includes a light-emitting unit which provides light having, a predetermined wavelength to a filter adsorbs foreign materials, a light-receiving unit which receives light reflected by the filter and convert reflected light information into a digital code to output, and a contamination calculating unit which processes the digital code provided by the light-receiving unit and calculates a degree of contamination of the filter, wherein the contamination calculating unit calculates a degree, in which a wavelength of the light reflected by the filter is shifted from the predetermined wavelength, compares intensity of light provided by the light-emitting unit with intensity of the light reflected by the filter, and calculates the degree of contamination of the filter.

7 Claims, 5 Drawing Sheets

(51) Int. Cl.
*B01D 46/00* (2006.01)
*G01N 21/25* (2006.01)
(52) U.S. Cl.
CPC .... *B01D 2273/26* (2013.01); *G01N 2201/062* (2013.01); *G01N 2201/123* (2013.01)

(56) References Cited

U.S. PATENT DOCUMENTS

2007/0013910 A1* 1/2007 Jiang .................. G01N 15/0205
356/336
2014/0185044 A1* 7/2014 Ishikawa ............ G01N 21/8806
356/369

FOREIGN PATENT DOCUMENTS

KR 10-1999-0019552 A 3/1999
KR 10-0909065 B1 7/2009

\* cited by examiner

APPARATUS AND METHOD FOR MEASURING CONTAMINATION OF FILTER

CROSS-REFERENCE TO PRIOR APPLICATION

This application claims priority to and the benefit of Korean Patent Application No. 10-2014-0116761, filed on Sep. 3, 2014, the disclosure of which is incorporated herein by reference in its entirety.

BACKGROUND

1. Field of the Invention

The present invention relates to an apparatus and method for measuring contamination of a filter.

2. Discussion of Related Art

Air filters are widely used in household and industrial facilities such as for household vacuum cleaners, air filters for automobiles, and air showers in semiconductor manufacturing systems, and the like. The air filter is disposed in a path to which intake air is supplied to filter foreign materials included in the intake air and purify the intake air.

The end-of-life filter does not serve as a filter due to reduction of the degree of purification in which the foreign materials included in the intake air are filtered, and thus does not filter the intake foreign materials to output. Therefore, the end-of-life filter may generate defects on semiconductor wafers manufactured in the semiconductor manufacturing systems, cause breakdown of car engines, further lead to respiratory disease caused by dust output from the vacuum cleaners, and thus a method and apparatus capable of measuring the degree of contamination of the air filter are required.

There is a related document, Korean Patent No. 0909065 which relates to a contamination measuring apparatus of an air filter according to the conventional technique.

SUMMARY OF THE INVENTION

The air filter contamination measuring apparatus according to the conventional technique irradiated one surface of the air filter with light having a sufficient wavelength to pass through the air filter, detected intensity of the light transmitted to an opposite surface, and then measured an amount of foreign materials adsorbed into the air filter and a degree of contamination of the air filter.

However, since the an filter contamination measuring apparatus according to the conventional technique uses a method for detecting the intensity of the light passing through the air filter, there is no difference between intensity of the emitted light and intensity of the reflected light when the amount of the foreign materials adsorbed into the air filter is very little, and thus the apparatus has a problem in that a degree of adsorption of the foreign materials into the air filter may not be sufficiently determined. Therefore, there is a problem in that the degree of contamination of the air filter may not be sufficiently determined.

Further, the light-receiving device used in the air filter contamination measuring apparatus according to the conventional technique, which is a luminosity sensor using cadmium sulfide (CdS), mainly uses cadmium that contaminates the environment as a main material, and thus it may cause an environmental contamination problem when the light-receiving device is manufactured or discarded.

According to an aspect of the present invention, there is provided a filter contamination measuring apparatus including: a light-emitting unit which provides light having a predetermined wavelength to a filter which adsorbs foreign materials; a light-receiving unit which receives light reflected by the filter and convert reflected light information into a digital code to output; and a contamination calculating unit which processes the digital code provided by the light-receiving unit and calculates a degree of contamination of the filter, wherein the contamination calculating unit calculates a degree, in which a wavelength of the light reflected by the filter is shifted from the predetermined wavelength, compares intensity of light provided by the light-emitting unit with intensity of the light reflected by the filter, and calculates the degree of contamination of the filter.

According to another aspect of the present invention, there is provided a filter contamination measuring method including: irradiating a filter with light; receiving light reflected by the filter; outputting digital codes corresponding to the intensity of the received reflected light and a wavelength of the reflected light; and calculating a degree of contamination of the filter using the digital codes, wherein the calculating of the degree of contamination of the filter includes calculating a degree, in which a wavelength of light emitted to the filter is shifted by being reflected by the filter, comparing intensity of the light emitted to the filter with intensity of the light reflected by the filter, and calculating the degree of contamination of the filter.

According to still another aspect of the present invention, there is provided a filter contamination measuring apparatus including: a light-emitting unit which irradiates at least a portion of a surface of a filter with light; a light-receiving unit which receives light reflected by the surface of the filter; a contamination determining unit which compares a wavelength of the light emitted from the light-emitting unit with a wavelength of the light reflected by the surface of the filter, compares intensity of the light emitted from the light-emitting unit with intensity of the light reflected by the surface of the filter, and determines a degree of contamination of the filter; and an alarm unit which notifies when the degree of contamination of the filter is greater than a predetermined threshold.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

The descriptions of the invention are only exemplary embodiments of the invention. The scope of the invention is not to be construed as being limited to the exemplary embodiments described herein. That is, while the invention is susceptible to various modifications and alternative forms, it should be understood that the invention is to cover all modifications, equivalents, and alternatives falling within the spirit and scope of the invention.

Meanwhile, it should be understood that the terms used herein are defined as follows.

It will be understood that, although the terms first, second, etc may be used herein to describe various elements, these elements should not be limited by these terms. These terms are only used to distinguish one element from another. For example, a first element could be termed a second element, and, similarly, a second element could be termed a first element, without departing from the scope of the present invention.

It will be understood that when an element is referred to as being "ontop" or "on" another element, it can be directly on the other element or intervening elements may be present. On the other hand, when an element is referred to as being "in contact with" another element, there are no intervening elements present. Meanwhile, other words used to describe the relationship between elements should be interpreted in a like fashion (i.e., "between" versus "directly between," "adjacent" versus "directly adjacent," etc.).

Elements of the invention referred to in singular may be number one or more, unless the context clearly indicates otherwise. It will be further understood that the terms "comprises," "comprising," "include" and/or "including," when used herein, specify the presence of stated features, numbers, steps, operations, elements, components, and/or groups thereof, but do not preclude the presence or addition of one or more other features, numbers, steps, operations, elements, components, and/or groups thereof.

Each of the steps can be differently performed from the specified order, unless the context clearly describes to a certain sequence. That is, each of the steps can be performed in the same manner as the specified order, substantially simultaneously performed with the specified order, and performed in the opposite order.

A size, height, or thickness of the elements in the accompanying drawings for describing the embodiments of the invention may be intentionally exaggerated for convenience of description and easy understanding, and are neither enlarged nor reduced according to the ratio. Further, any element shown in the drawings can be intentionally reduced, and the other elements can be intentionally enlarged.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 1:
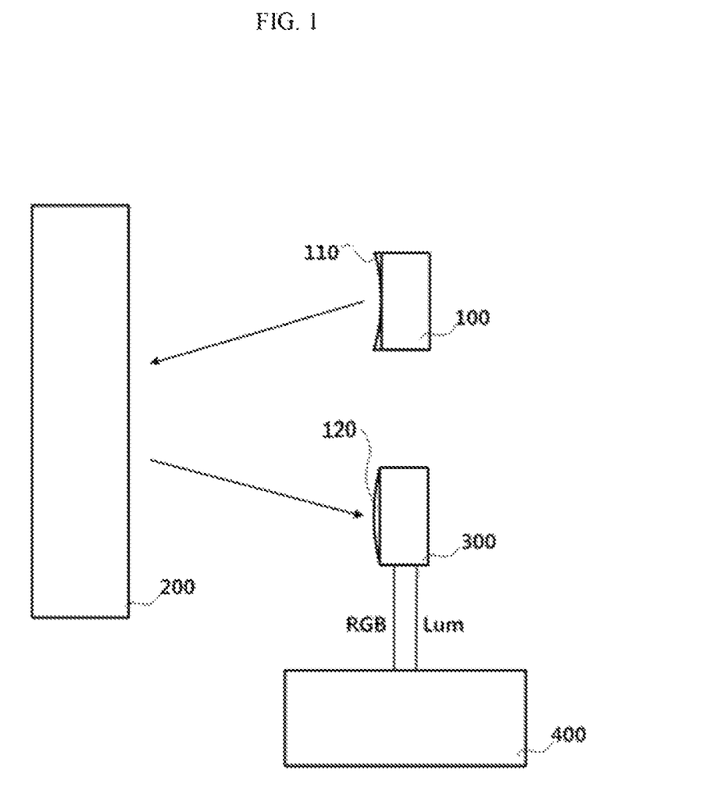
FIG. 1 is a view showing a filter contamination measuring apparatus according to an embodiment of the present invention.
Figure 2:
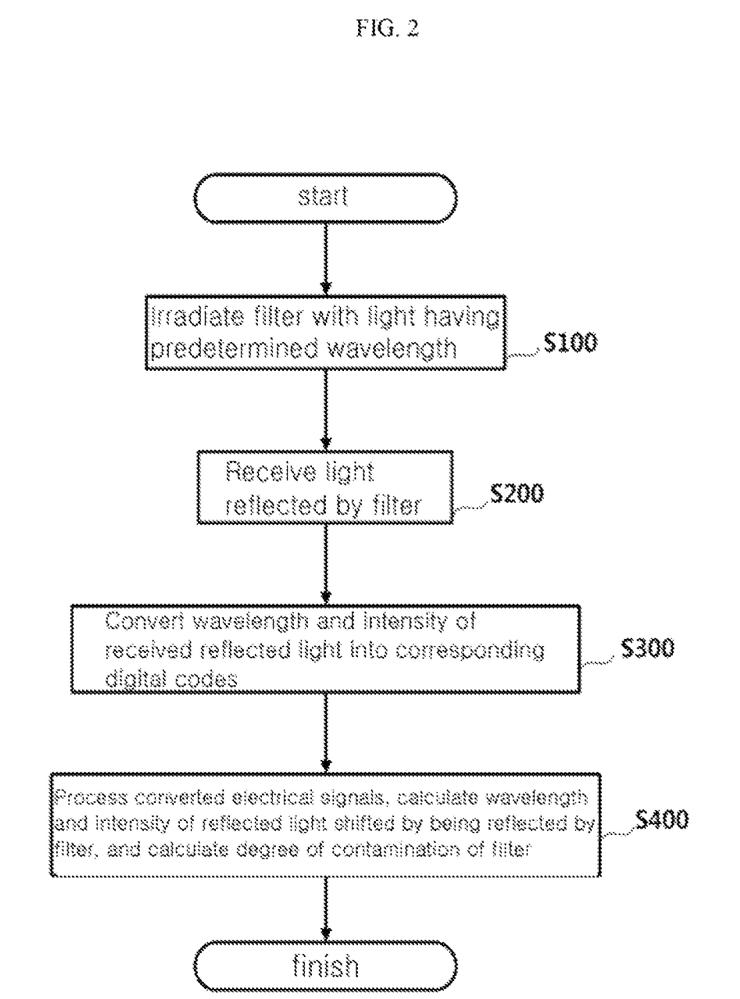
FIG. 2 is a flowchart showing an overview of a fitter contamination measuring method according to the embodiment of the present invention.

Hereinafter, a filter contamination measuring apparatus and a filter contamination measuring method according to an embodiment of the present invention will be described with reference to the accompanying drawings. FIG. 1 is a view showing, a filter contamination measuring apparatus according to an embodiment of the present invention. FIG. 2 is a flowchart showing an overview of a filter contamination measuring method according to the embodiment of the present invention. Referring to FIGS. 1 and 2, a light-emitting unit 100 provides light haying a predetermined wavelength to a filter which adsorbs foreign materials. In the embodiment, the light-emitting unit 100 includes a light-emitting diode (LED) and provides visible rays having the predetermined wavelength to at least one portion of a surface of a filter 200. For example, the light-emitting unit 100 provides visible rays having a wavelength in a range of 400 nm to 500 nm to the filter 200.

In general, a wavelength in a range of 380 nm to 430 nm corresponds to violet color, a wavelength in a range of 430 nm to 520 nm corresponds to blue color, a wavelength in a range of 520 nm to 565 nm corresponds to green color, and a wavelength in a range of 565 nm to 600 nm corresponds to one of yellow color and orange color. However, since the color is not discontinuously changed according to a change of the above-described wavelength but continuously changed according to the change of the wavelength, the wavelength and the color according thereto refers to a representative color of the corresponding wavelength to help understanding of the present invention and it should be understood that the scope of the present invention is not limited or restricted thereto.

For example, it may be difficult that the light provided by the light-emitting unit 100 is uniformly emitted to the surface of the filter 200, and particularly, when mountain regions and valley regions are formed in the filter 200, the light may not uniformly emitted to the surface of the filter 200. When a first lens 110 is disposed on a surface of the light-emitting unit 100, light provided by the LED may be divided and the divided light may uniformly emitted to the surface of the filter 200.

Since light reflected by the surface of the filter 200 is diffused due to foreign materials adsorbed into the filter 200 to uniformly progress in all directions, light collecting efficiency may be reduced when a light-receiving diode is simply disposed and receives the light reflected by the surface of the filter 200. In this case, a second lens 120 which collects the reflected light into a light-receiving unit 300 is disposed and the light-receiving unit 300 receives the collected reflected light, and thus the light collecting efficiency can be improved.

Although it is shown that the first lens 110 is a concave lens and the second lens 120 is a convex lens, it is only an example and the first lens 110 and the second lens 120 are not limited to the convex lens and the concave lens. A lens which uniformly emits light by dividing the light may be used for the first lens 110 and a lens which collects the light may be used for the second lens 120. For example, the first lens 110 and the second lens 120 may be formed with a Fresnel lens.

The filter 200 adsorbs foreign materials included in intake air and filters the foreign materials. In general, a surface area of the filter 200 in contact with the air is largely formed in order to improve a filtration rate of the foreign materials. For example, the filter 200 is formed with fine fibers or so as to have mountain regions and valley regions, and thus an area in contact with the air may be largely formed. For example, the filter 200 may be a high efficiency particulate air (HEPA) filter capable of filtering 99.97% of particles of 0.3 $\lambda$m.

The light-receiving, unit 300 receives the light reflected by the filter 200 and converts the received light into electrical signals to output. For example, the light-receiving unit 300 may include a color sensor 310 and an ambient light sensor (ALS) 320. For example, the color sensor 310 detects light of red, green, and blue wavelengths, and outputs a digital code RGB corresponding to a wavelength of the received light. The ALS 320 outputs a digital code Lum corresponding to intensity of detected light.

Figure 3A:
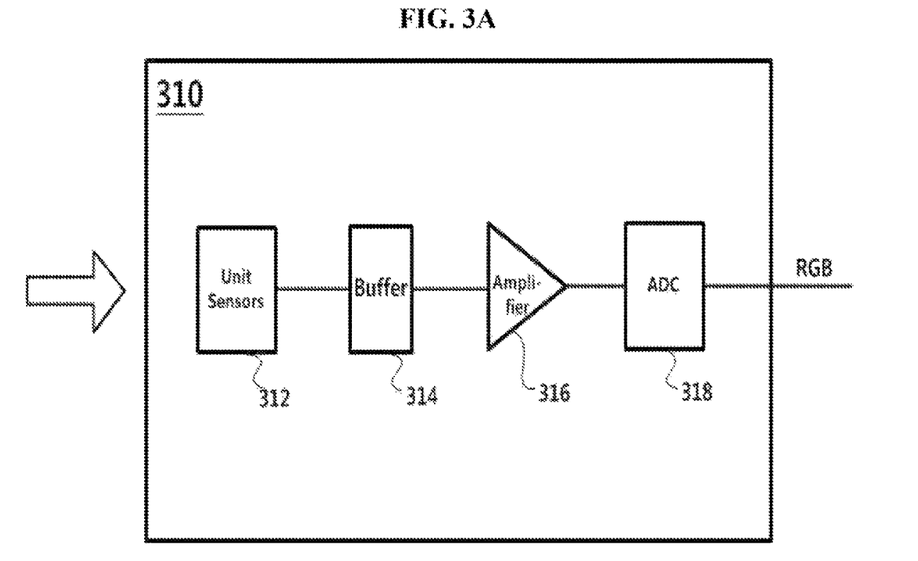
FIG. 3A is a view showing an example of a color sensor and FIG. 3B is a view showing an example an ambient light sensor.

FIG. 3A is a view showing an example of the color sensor 310. FIG. 3B is a view showing an example of the ALS 320. Referring to FIG. 3A, the color sensor 310 according to the embodiment of the present invention includes each of unit sensors 312 which detects light of red, green, and blue wavelengths to output as electrical signals, a buffer 314 which receives the electrical signals output from the unit sensors 312, an amplifier 316 which amplifies the electrical signals output from the buffer 314, and an analog-to-digital convener (ADC) 318 which receives the amplified electrical signals and converts the signals into the digital codes RGB corresponding thereto to output. In another embodiment, the color sensor 310 may further include a unit sensor which detects white light in addition to the unit sensors 312 which detect the light of red, green, and blue wavelengths.

Figure 3B:
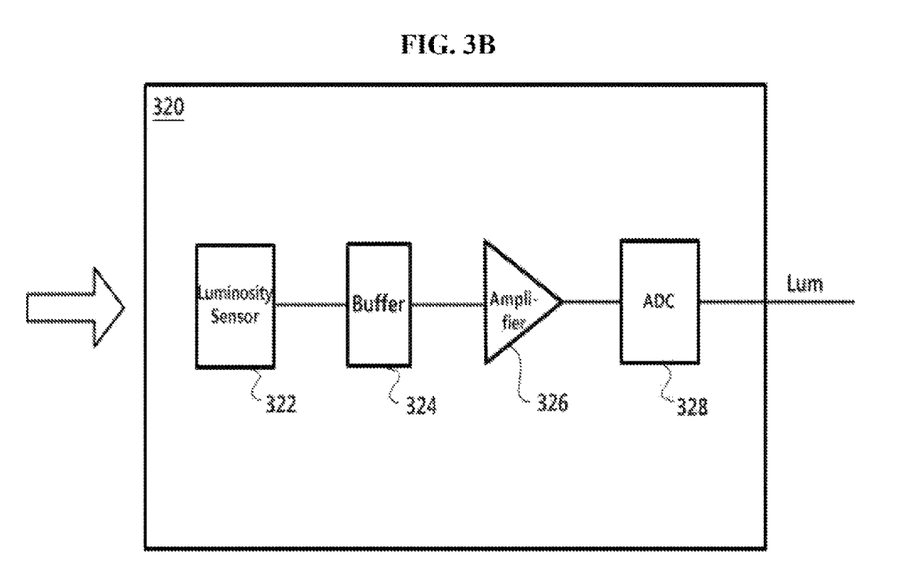

Referring to FIG. 3B, the ALS 320 according to the embodiment of the present invention includes a luminosity sensor 322 which detects intensity of the received light to output as electrical signals, a buffer 324 which receives the electrical signals output from the luminosity sensor 322, an amplifier 326 which amplifies the electrical signals output from the buffer 324, and an ADC 328 which receives the amplified electrical signals and converts the signals into the digital codes Lum corresponding thereto to output.

According to another embodiment, not shown, unlike the above embodiment, using one ADC having a plurality of input ports and output ports, output signals of the amplifier 316 included in the color sensor 310 and output signals of the amplifier 326 included in the ALS 320 are input into each of the input ports, and converted digital codes are output to separate output ports.

Since the color sensor 310 and the ALS 320 each provide information about the detected wavelength and the intensity of the received light to a contamination calculating unit 400 in the digital code form, the contamination calculating unit 400 may obtain the information about the wavelength of the reflected light and the intensity of the reflected light therefrom.

In an embodiment, the color sensor 310 and the ALS 320 may be respectively implemented to configure the light-receiving unit 300. In another embodiment, the color sensor 310 and the ALS 320 may be implemented in a single module to configure the light-receiving unit 300.

A conventional luminosity sensor includes cadmium sulfide CdS), cadmium is fatal to humans when the human body is poisoned by cadmium and is able to contaminate the environment, and thus its use is strictly limited. Since the ALS 320 according to the embodiment of the present invention uses a luminosity sensor that does not contain cadmium sulfide (CdS), the ALS 320 does not any cause cadmium poisoning and environmental contamination problem.

The contamination calculating unit 400 processes the digital codes RGB and Lum provided by the light-receiving unit 300 to calculate a degree of contamination of the filter 200. For example, the contamination calculating unit 400 includes a calculating unit 440 (not shown), which calculates the wavelength of the reflected light and the intensity of the reflected light using the digital codes RGB and Lum provided by the light-receiving unit 300, obtains a wavelength shift formed by reflecting the wavelength of the light provided by the light-emitting unit 100 to the filter 200 and intensity of the shifted wavelength, and then calculates the degree of contamination of the filter 200.

For example, the filter contamination measuring apparatus and the filter contamination measuring method according to the embodiment of the present invention further includes an alarm unit (not shown) which provides alarm signals to the user according to the degree of contamination of the filter 200 calculated in the contamination calculating unit 400. The alarm unit may include at least one of an LED, which receives control signals from the contamination calculating unit 400 and provides visual alarm signals to the user, and a speaker which provides audible alarm signals.

Figure 4:
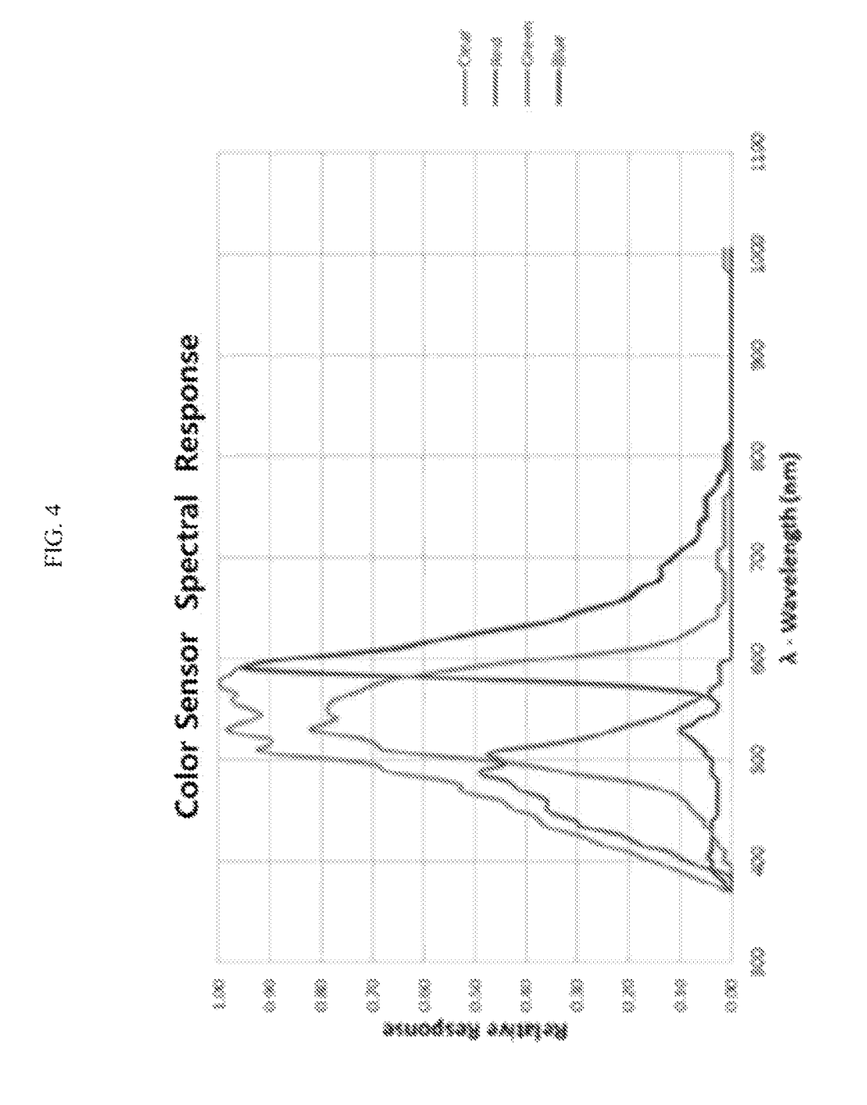
FIG. 4 is a graph showing a response of a color sensor in a light-receiving unit with respect to a wavelength of emitted light and relative responses of unit sensors with respect to blue, green, red, and white light.
Figure 5:
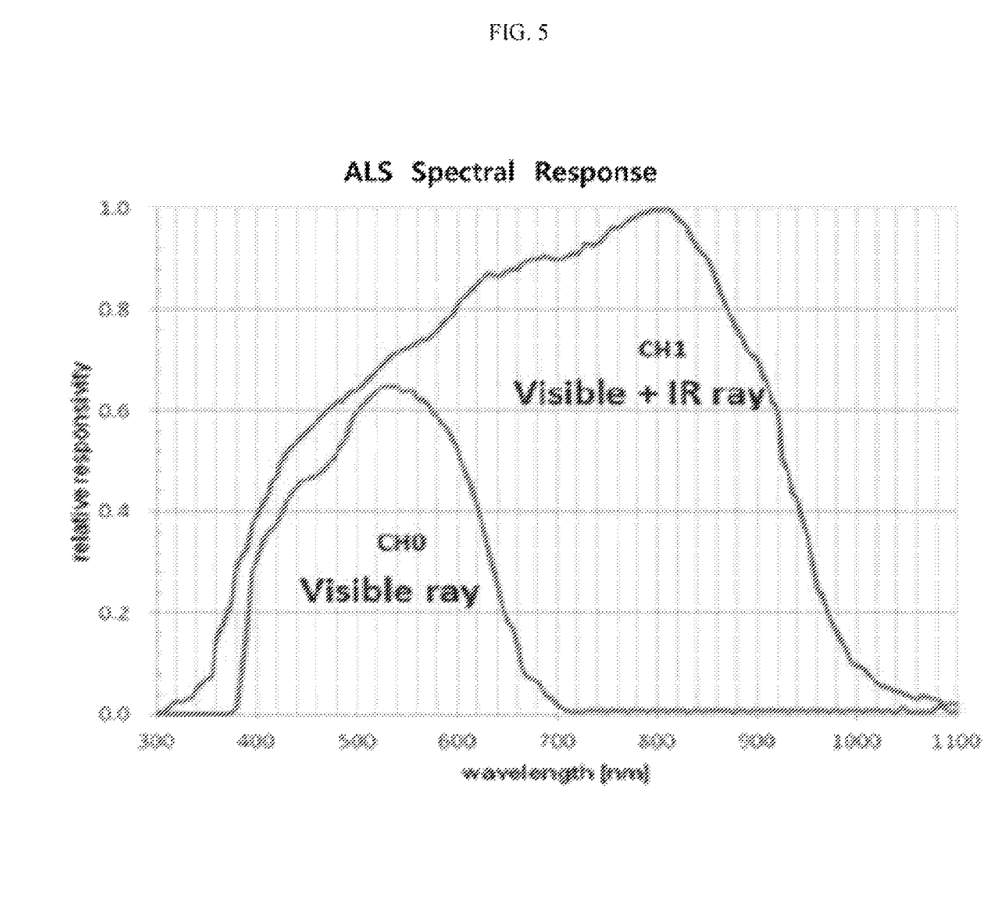
FIG. 5 is a graph showing a response of an ambient light sensor in a light-receiving unit with respect to a wavelength of emitted light.

Hereinafter, operations of the filter c on lamina bon measuring apparatus including the above components and processes of the filter contamination measuring method will be described. The light-emitting unit 100 irradiates the filter 200 with light (S100). FIG. 4 is a graph showing a response of the color sensor 110 with respect to light received by the light-receiving unit 300, and relative responses of the unit sensors 312 with respect to blue, green, red, and white light. FIG. 5 is a graph showing a response of the ambient light sensor 320 with respect to a wavelength of the light received by the light-receiving unit 300.

Referring to FIG. 4, it may be seen that when a wavelength of light received by the color sensor 310 is in the vicinity of 400 nm, responses with respect to blue light and white light are increased, when the wavelength of the light is in the vicinity of 500 nm, a response with respect to green light is increased, when the wavelength of the light is in the vicinity of 550 nm, a response with respect to red light is increased, and when the wavelength of the light is in a range of 600 nm or more, a response is decreased. That is, it may be seen that the color sensor 310 may sensitively detect light of a wavelength in a range of 400 nm to 600 nm compared with the other wavelengths.

Referring to FIG. 5, it may be seen that a response of the ALS 320 is increased in the vicinity of a wavelength of 400 nm of visible rays, and is reduced as a wavelength is increased from 600 nm. Therefore, it may be seen that the ALS 320 may also sensitively detect light of a wavelength in a range of 400 nm to 600 nm in the same manner as the color sensor 310.

Therefore, when the light-emitting unit 100 irradiates the filter 200 with light, the light is reflected due to the foreign materials adsorbed into the filter 200. When a wavelength of the reflected light is shifted from the wavelength of the light provided by the light-emitting unit 100 to the wavelength in a range of 400 nm to 600 nm, it may be determined that the foreign materials are adsorbed into the filter 200 with high sensitivity and resolution. Further, when the light emitted by the light-emitting unit 100 is absorbed into the foreign materials adsorbed into the filter 200 and intensity of the light is reduced, the ALS 320 may sensitively detect a change of the intensity of the light.

The light-receiving unit 300 receives the light reflected by the filter 200 (S200) and converts the received light into electrical signals corresponding to the wavelength (S300). For example, the light-receiving unit 300 includes the color sensor 310 an the ALS 320, and thus the light-receiving unit 300 outputs the digital codes RGB and Lum corresponding to the wavelength and the intensity included in the incident light to provide to the contamination calculating unit 400.

The contamination calculating unit 400 calculates the degree of contamination of the filter 200 using the digital code RGB having wavelength information of the reflected light. provided by the light-receiving unit 300 and the digital code Lum having intensity information of the reflected light (S400). For example, the light incident on the light-receiving unit 300 is light in which the light emitted by the light-emitting unit 100 is reflected by the filter 200, and the wavelength of the reflected light may be shifted by a color of a reflective surface. For example, when sunlight is reflected by a blue reflective surface, the wavelength of the reflected light is shifted to a range corresponding to blue color, and when the sunlight is reflected by a red reflective surface, the wavelength of the reflected light is shifted to a range corresponding to red color.

Therefore, the emitted light in the known wavelength is emitted to the filter 200 and the wavelength of the light reflected by the filter 200 is detected. When the detected wavelength is compared with the wavelength of light provided by the light-emitting unit 100, wavelength changes before and after the reflection may be determined. Therefore, when the digital codes RGB and Lum provided by the light-receiving unit 300 are used, whether the foreign materials which shifts the wavelength of the emitted light are adsorbed into the filter 200 or not may be determined.

For example, when the light emitted by the light-emitting, unit 100 has a wavelength of 450 nm and the light reflected by the filter 200 includes light having a wavelength of 550 nm, it means that the light is shifted to have a long wavelength while the light is reflected by the filter 200. Therefore, it may be determined that the foreign materials which shift the emitted light to have the long wavelength are adsorbed into the filter 200.

Further, when the reflected light has intensity of light having, a wavelength of 450 nm dominant compared with intensity of the other wavelengths, it may be determined that a large amount of the foreign materials which shift the wavelength of the emitted light are not adsorbed into the filter 200 and thus a degree of contamination of the filter 200 is low. On the other hand, when the reflected light has intensity of light having a wavelength of 550 nm dominant compared with intensity of light, which is the emitted light, having a wavelength of 450 nm, it may be determined that a large amount of the foreign materials which shift the wavelength of the emitted light to have a long wavelength are adsorbed into the filter 200 and thus the degree of contamination the filter 200 is high.

Further, air cleaners used at home and air filters used in automobiles adsorb dust to filter the air. The dust is adsorbed into the surface of the filter and generally represents an achromatic color such as gray. A change of a wavelength of light, in which light emitted to the filter 200 to which the achromatic colored dust is adsorbed is reflected, is not significant compared with that of the wavelength of the emitted light, in a similar manner that a wavelength of light in which light emitted to a white surface is reflected is not significantly different from the wavelength of the emitted light, and thus it may be difficult to measure the degree of contamination of the filter 200 using the color sensor 310.

However, as an amount of the foreign materials of the achromatic color adsorbed into the filter 200 is increased, the reflective surface which reflects the emitted light is changed to gray color, the emitted light is absorbed by the foreign materials, and thus intensity of the reflected light is less than the intensity of the emitted light. Therefore, the intensity of the reflected light is detected using the ALS 320, the intensity of the emitted light provided by the light-emitting, unit 100 and the intensity of the reflected light are compared, and thus an amount of the foreign materials of the achromatic color adsorbed into the surface of the filter 200 may be also determined with high resolution. Therefore, the degree of contamination of the filter 200 may be more accurately calculated.

As described above, the color sensor 310 and the ALS 320 included in the light receiving unit 300 may measure light of a wavelength in a range of 400 nm to 600 nm compared with light in the other wavelengths with high sensitivity. For example, when the light-emitting unit 100 irradiates the filter 200 with monochromatic light having a wavelength of 450 nm and the reflected light includes the reflected light component shifted to have a long wavelength in a range of 500 nm to 600 nm and the reflected light component having a wavelength of 450 nm, the degree of contamination of the filter 200 is differently calculated according to a ratio of the intensity of the reflected light shifted to have the long wavelength and the intensity of the reflected. light having the wavelength of 450 nm. The light-receiving unit 300 according to the embodiment of the present invention may detect light of the wavelength in a range of 400 nm to 600 nm with high sensitivity compared with those of the other wavelengths, and thus the degree of contamination of the filter 200 may be accurately measured.

Further, when the degree of contamination of the filter 200 is measured using a difference between the intensity of the emitted light provided by the light-emitting unit 100 and the intensity of the reflected light, the wavelength of the light provided by the light-emitting unit 100 is included in a wavelength sensitively detected by the ALS 320 included in the light-receiving unit 300, and thus the degree of contamination of the filter 200 may be measured with high accuracy.

However, in the embodiment in which the intensity of the reflected light is measured using the ALS 320, although it is described that the foreign materials are adsorbed to form the reflective surface of the achromatic color, the case in that the foreign materials are adsorbed to form the reflective surface having color may be also applied. For example, when nicotine and tar are adsorbed into the surface of the filter 200 from tobacco smoke and the color of the filter 200 is changed to dark brown color, in addition to a shift of the wavelength of the reflected light, intensity of the light reflected by the dark brown colored surface is less than the intensity of the light emitted by the light-emitting unit 100. Therefore, the contamination calculating unit 400 receives the digital code Lum detected and provided by the ALS 320, compares the digital code Lum with the intensity of the emitted light, and thus the degree of contamination of the filter 200 may be calculated.

For example of calculating the degree of contamination of the filter 200, the contamination calculating unit 400 receives the digital code Lum, which is determined and provided by the ALS 320 and corresponds to the intensity of the reflected light, compares the digital code Lum with the intensity of the emitted light, and thus the degree of contamination of the filter 200 may be calculated. Further, the contamination calculating unit 400 receives the digital code RGB provided by the color sensor 310 and may calculate a shifted degree of the wavelength and the intensity of the shifted wavelength using a predetermined look up table or a pre-programmed formula to calculate the degree of contamination of the filter 200.

In another embodiment, as an example, the contamination calculating unit 400 may obtain a difference between the wavelength of the emitted light and the wavelength of the reflected light to obtain a shift of the wavelength of the emitted light and the wavelength of the reflected light. As another example, the contamination calculating unit 400 may calculate a ratio of the wavelength of the emitted light and the wavelength of the reflected light to obtain the shift between the wavelength of the emitted light and the wavelength of the reflected light. Further, as an example, the contamination calculating unit 400 may obtain a difference value between the intensity of the emitted light and the intensity of the reflected light to obtain a difference between the intensity of the emitted light and the intensity of the reflected light. As another example, the contamination calculating unit 400 may calculate a ratio of the intensity of the emitted light and the intensity of the reflected light to obtain the difference between the intensity of the emitted light and the intensity of the reflected light.

The contamination calculating unit 400 calculates the difference between the wavelengths of the emitted light and the reflected light or the ratio of the shifted wavelengths of the emitted light and the reflected light, and the difference between the intensity of the emitted light and the reflected light or the intensity ratio of the emitted light and the reflected light obtained in the above-described manner using the predetermined look up table or the pre-programmed formula to calculate the degree of contamination of the filter 200.

In an embodiment, when the degree of contamination of the filter 200 obtained in the above-described manner is more than a predetermine threshold, the contamination calculating unit 400 may further include an alarm unit (not shown) which provides alarm signals to the outside. Further, the alarm unit may he implemented so as to generate different alarms according to the degree of contamination of the filter 200.

According to the embodiment of the present invention, the wavelength of the emitted light is compared with the wavelength of the reflected light, the intensity of the emitted light is compared with the intensity of the reflected light, and thus a degree in which the foreign materials are adsorbed into the filter 200 is determined. Therefore, the degree of the adsorption of the foreign materials to the filter 200 is determined using two different methods, and thus the degree of the adsorption of the foreign materials to the filter 200 may be determined with higher reliability.

According to the embodiment of the present invention, a wavelength of the reflected light, in which the emitted light in a known wavelength is reflected and shifted by the filter, is detected, a shift of the wavelength and intensity of the light in the shifted wavelength are calculated, a degree of adsorption of foreign materials into the filter is determined, intensity of the emitted light and intensity of the reflected light are compared, and thus the degree of contamination of the filter may be determined.

Therefore, according to the embodiment of the present invention, the amount of the foreign materials adsorbed into the filter may he determined using different two methods. The embodiments of the present invention provides advantages in which the degree of contamination of the filter may be measured with high reliability compared. with the titter contamination measuring apparatus and the filter contamination measuring method according to the conventional technique.

As described above, while the specific specification and drawings describe exemplary embodiments of the invention, the invention is not limited thereto. It is apparent to those skilled in the art that various modifications and alterations can be made within the technological scope of the invention and equivalents of the appended claims to be described below.

What is claimed is:

1. A filter contamination measuring apparatus, comprising:
   a light-emitting unit configured to provide a first light having a predetermined wavelength to a filter configured to adsorb foreign materials;
   at least one sensor configured to receive a second light reflected by the filter, convert information of the second light into a digital code, and output the digital code; and
   a processor configured to calculate wavelength and intensity of the second light by processing the digital code provided by the at least one sensor and calculate a degree of contamination of the filter,
   wherein the processor calculates the degree of contamination of the filter based on a wavelength shifting value which is calculated by comparing the wavelength of the second light with the predetermined wavelength of the first light, and an intensity variation value which is calculated by comparing the intensity of the second light with an intensity of the first, and
   wherein the wavelength shifting value includes a difference between the predetermined wavelength of the first light and the wavelength of the second light or a ratio of the wavelength of the second light to the predetermined wavelength of the first light, and the intensity variation value includes a difference between the intensity of the first light and the intensity of the second light or a ratio of the intensity of the second light to the intensity of the first light.

2. The apparatus of claim 1, further comprising:
   a first lens configured to uniformly irradiate the filter with the light provided by the light-emitting unit; and
   a second lens configured to collect the light reflected by the filter and irradiate the at least one sensor with the collected light.

3. The apparatus of claim 1, wherein the at least one sensor comprises:
   a color sensor configured to detect light of red, green, and blue wavelengths and output electrical signals corresponding to the detected wavelengths; and
   an ambient light sensor (ALS) configured to detect light intensity.

4. The apparatus of claim 3, wherein the color sensor comprises:
   unit sensors configured to detect light of red, green, and blue wavelengths;
   an amplifier configured to amplify signals output from the unit sensors; and
   an analog-to-digital converter (ADC) configured to convert signals output from the amplifier into digital codes, and
   wherein the ambient light sensor comprises:
   a luminosity sensor configured to detect intensity of received light;
   an amplifier configured to amplify a signal output from the luminosity sensor; and
   an ADC configured to convert a signal output from the amplifier into a digital code.

5. The apparatus of claim 1, wherein the light-emitting unit provides light of a wavelength in a range of 400 nm to 500 nm.

6. The apparatus of claim 1, wherein the at least one sensor has sensitivity with respect to light of a wavelength in a range of 400 nm to 600 nm higher than those of the other wavelengths.

7. The apparatus of claim 1, wherein the filter is a high efficiency particulate air (HEPA) filter.

* * * * *